(12) United States Patent
Toda et al.

(10) Patent No.: US 9,301,908 B2
(45) Date of Patent: Apr. 5, 2016

(54) DETERGENT COMPOSITION

(75) Inventors: Tomoko Toda, Sakai (JP); Uhei Tamura, Ibaraki (JP); Yoshinobu Saito, Ibaraki (JP); Yumiko Takeda, Ibaraki (JP); Saori Kajita, Ibaraki (JP); Tetsuo Nishina, Takatsuki (JP)

(73) Assignee: P & PF Co., Ltd., Osaka (JP)

( * ) Notice: Subject to any disclaimer, the term of this patent is extended or adjusted under 35 U.S.C. 154(b) by 0 days.

(21) Appl. No.: 14/237,380

(22) PCT Filed: Aug. 28, 2012

(86) PCT No.: PCT/JP2012/071682
§ 371 (c)(1),
(2), (4) Date: Feb. 6, 2014

(87) PCT Pub. No.: WO2013/031762
PCT Pub. Date: Mar. 7, 2013

(65) Prior Publication Data
US 2014/0194334 A1      Jul. 10, 2014

(30) Foreign Application Priority Data

Aug. 30, 2011  (JP) ................................ 2011-187912

(51) Int. Cl.
| | | |
|---|---|---|
| *A61K 8/44* | (2006.01) | |
| *A61K 8/39* | (2006.01) | |
| *A61Q 19/10* | (2006.01) | |
| *C11D 3/48* | (2006.01) | |
| *C11D 1/94* | (2006.01) | |
| *A61K 8/49* | (2006.01) | |
| *A61Q 17/00* | (2006.01) | |
| *A61K 8/33* | (2006.01) | |
| *A61Q 5/02* | (2006.01) | |
| *A61K 8/898* | (2006.01) | |
| *C11D 1/72* | (2006.01) | |
| *C11D 1/90* | (2006.01) | |

(52) U.S. Cl.
CPC .... *A61K 8/44* (2013.01); *A61K 8/33* (2013.01); *A61K 8/39* (2013.01); *A61K 8/4946* (2013.01); *A61K 8/898* (2013.01); *A61Q 5/02* (2013.01); *A61Q 17/005* (2013.01); *A61Q 19/10* (2013.01); *C11D 1/94* (2013.01); *C11D 3/48* (2013.01); *C11D 1/72* (2013.01); *C11D 1/90* (2013.01)

(58) Field of Classification Search
CPC ....................................................... A61K 8/44
USPC ......................................................... 510/160
See application file for complete search history.

(56) References Cited

U.S. PATENT DOCUMENTS

| | | | | |
|---|---|---|---|---|
| 5,527,492 | A * | 6/1996 | Hayakawa ..................... | 510/131 |
| 6,338,855 | B1 * | 1/2002 | Albacarys et al. ............. | 424/409 |
| 2003/0180231 | A1 * | 9/2003 | Danoux et al. ................. | 424/59 |
| 2005/0095215 | A1 * | 5/2005 | Popp ........................... | 424/70.21 |
| 2005/0100621 | A1 * | 5/2005 | Popp et al. .................... | 424/776 |
| 2006/0264344 | A1 * | 11/2006 | Goldberg et al. ............. | 510/130 |
| 2006/0264505 | A1 * | 11/2006 | Popp et al. .................... | 514/547 |
| 2010/0254928 | A1 * | 10/2010 | Yamazaki et al. ........... | 424/70.1 |
| 2011/0118164 | A1 * | 5/2011 | Kimura et al. ................ | 510/130 |
| 2014/0194334 | A1 * | 7/2014 | Toda et al. ..................... | 510/160 |

FOREIGN PATENT DOCUMENTS

| | | | |
|---|---|---|---|
| JP | 54-049322 | | 4/1979 |
| JP | 02-245097 | | 9/1990 |
| JP | 05-097634 | | 4/1993 |
| JP | 2003-034661 | | 2/2003 |
| JP | 2005-206713 | | 8/2005 |
| JP | 2005-232011 | | 9/2005 |
| JP | 2007-131594 | | 5/2007 |
| JP | 2008-081600 | | 4/2008 |
| JP | 2008-144057 | | 6/2008 |
| JP | 2008-208323 | | 9/2008 |
| JP | 2008208323 | A * | 9/2008 |
| JP | 2009-132625 | | 6/2009 |

OTHER PUBLICATIONS

Patent Abstracts of Japan, Publication No. 2003-034661, 15 pages.
Patent Abstracts of Japan, Publication No. 2007-131594, 24 pages.
Patent Abstracts of Japan, Publication No. 2008-208323, 14 pages.
Patent Abstracts of Japan, Publication No. 2009-132625, 26 pages.
Patent Abstracts of Japan, Publication No. 2005-232011, 9 pages.
Patent Abstracts of Japan, Publication No. 2008-144057, 16 pages.
Patent Abstracts of Japan, Publication No. 2008-081600, 15 pages.
Patent Abstracts of Japan, Publication No. 54-049322, 1 page.
Patent Abstracts of Japan, Publication No. 05-097634, 9 pages.
Patent Abstracts of Japan, Publication No. 2005-206713, 15 pages.
Patent Abstracts of Japan, Publication No. 02-245097, 1 page.
PCT Notification of Transmittal of Translation of the International Preliminary Report on Patentability dated Mar. 13, 2014, 6 pages.

* cited by examiner

*Primary Examiner* — Mark Eashoo
*Assistant Examiner* — M. Reza Asdjodi
(74) *Attorney, Agent, or Firm* — Rankin, Hill & Clark LLP

(57) ABSTRACT

A detergent composition excellent in an antimicrobial activity. Thus, a detergent composition of the present invention is characterized by including:
an imidazolinium betaine-based amphoteric surfactant; and
0.5 to 10% by mass of PEG-1 lauryl glycol represented by the following formula (I):

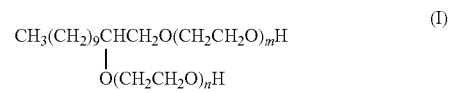

wherein, m and n each represent the number of moles of added ethylene oxide and the average of m+n is 1. Also, the detergent composition preferably includes an ingredient having a microstatic effect or microcidal effect selected from divalent glycols, hinokitiol, trichlorocarbanilide, and benzalkonium chloride.

15 Claims, No Drawings

DETERGENT COMPOSITION

RELATED APPLICATIONS

This application claims the priority of Japanese Patent Application No. 2011-187912 filed on Aug. 30, 2011, which is incorporated herein by reference.

FIELD OF THE INVENTION

The present invention relates to a detergent composition and particularly to the improvement of antimicrobial activity (against bacteria and fungi) thereof.

BACKGROUND OF THE INVENTION

In recent years, many people have kept animals such as dogs and cats indoors, and bathing of such pet animals has been performed routinely. Thus, various shampoos suitable for use on hair coats of pet animals have been developed. For example, there are some shampoos comparable or superior to those for human in terms of good sense of use, such as foaming properties, shininess, and smoothness.

In contrast, in the case of dogs, cats and the like, dermatoses are often caused by bacteria, fungi and the like adhered to their hair coats. Additionally, ears of such animals are easily subject to invasion by fungi due to the structure, and are also liable to develop otitis externa. Therefore, shampoos for animals are typically required to have effects comparable or superior to those for human also in an antimicrobial activity (against bacteria and fungi).

Also in patients with human atopic dermatitis, infectious disease complications due to growth of bacteria on skin have become a problem.

As a common means to impart an antimicrobial activity to a detergent composition such as shampoos, irrespective of subjects on which the compositions are used, it is contemplated to use antimicrobial ingredients (preservatives or microcidal agents) blended in cosmetics to prevent deterioration of the products, such as benzoic acid, sodium benzoate, para-hydroxybenzoic acid esters (parabens), sorbic acid, dehydroacetic acid, phenoxyethanol, benzalkonium chloride, benzethonium chloride, and chlorohexidine.

However, since each of these ingredients has problems such as strong irritation to the skin and eyes and allergies, the amount that can be blended is limited. Thus, it was difficult to provide the subjects with a sufficient antimicrobial activity by use of shampoos.

For such problems, as a microcidal agent that can be blended to pharmaceuticals, cosmetics, and foods and that provides a potent effect in a small amount, an antiseptic microcidal agent containing, for example, 1,2-alkanediol and an imidazoline-based amphoteric surfactant is suggested (Patent Document 1).

Patent Document 1: Japanese Patent No. 4086794

DISCLOSURE OF THE INVENTION

Problem to be Solved by the Invention

However, a detergent composition that widely responds not only to bacteria and fungi associated with human infectious diseases, but also to bacteria and fungi adhering in a large amount to animal hair coats and causing dermatoses and otitis externa, and that has a potent antimicrobial activity has not yet been put into practical use.

The present invention has been made in view of the problems and seeks to provide a detergent composition excellent in an antimicrobial activity.

Means to Solve the Problem

As the result of intensive studies to solve the problems, the present inventors found that an imidazolinium betaine-based amphoteric surfactant and PEG-1 lauryl glycol are blended to provide a detergent composition excellent in an antimicrobial activity and having high safety, thereby completing the present invention.

Thus, a detergent composition of the present invention is characterized by comprising:

an imidazolinium betaine-based amphoteric surfactant; and 0.5 to 10% by mass of PEG-1 lauryl glycol represented by the following formula (I):

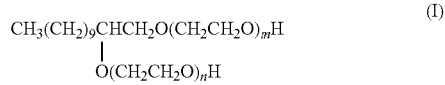

wherein, m and n each represent the number of moles of added ethylene oxide and the average of m+n is 1.

Also, in the detergent composition, it is preferable to further comprise an ingredient having a microstatic effect or microcidal effect selected from divalent glycols, hinokitiol, trichlorocarbanilide, and benzalkonium chloride.

Also, it is preferable that the detergent composition is used for animals.

Also, it is preferable that the detergent composition is used for patients with human atopic dermatitis.

Effect of the Invention

According to the present invention, it becomes possible to produce a detergent composition suitable for animals and for patients with human atopic dermatitis, wherein the detergent composition is low-irritant to the skin and eyes and excellent in an antimicrobial activity.

BEST MODE FOR CARRYING OUT THE INVENTION

Hereinbelow, suitable embodiments of the present invention will be described.

The detergent composition according to the present invention contains an imidazolinium betaine-based amphoteric surfactant and PEG-1 lauryl glycol. First, the ingredients will be described.

Imidazolinium Betaine-Based Amphoteric Surfactant

The imidazolinium betaine-based amphoteric surfactants that can be used for the present invention are not particularly limited as long as the surfactants are those usually used in cosmetics and quasi-pharmaceutical products. The example includes surfactants represented by the following formula (II).

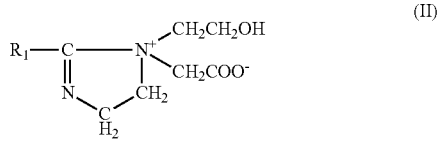

(II)

In the formula (II), $R_1$ represents a linear or branched alkyl group, alkenyl group or acyl group having 8 to 18, preferably 10 to 14 carbon atoms. Examples of the alkyl group include an octyl group, a nonyl group, a decyl group, an undecyl group, a dodecyl group, a tridecyl group, a tetradecyl group, a pentadecyl group, a hexadecyl group, a heptadecyl group, an octadecyl group, and a 2-ethylhexyl group. Examples of the alkenyl group include an octenyl group, a nonenyl group, a decenyl group, an undecenyl group, a dodecenyl group, a tetradecenyl group, and an oleyl group. Examples of the acyl group include a lauroyl group, a myristoyl group, a palmitoyl group, a stearoyl group, an oleoyl group, and a coconut oil fatty acid acyl group (a cocoyl group).

Examples of such imidazolinium betaine-based amphoteric surfactants include
N-lauroyl-N'-carboxymethyl-N'-hydroxyethylethyleneimidazoliniumbetaine,
N-cocoyl-N-carboxymethyl-N'-hydroxyethylethyleneimidazoliniumbetaine,
2-cocoyl-N-carboxymethyl-N-hydroxyethylimidazoliniumbetaine,
2-lauryl-N-carboxymethyl-N-hydroxyethylimidazoliniumbetaine
2-undecyl-N,N,N-(hydroxyethylcarboxymethyl)-2-imidazoliniumbetaine.

Alternatively, the imidazolinium betaine-based surfactant may be in the salt form represented by the following formula (III).

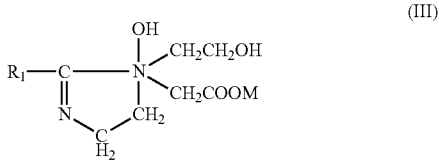

(III)

In the formula (III), $R_1$ represents a linear or branched alkyl group, alkenyl group or acyl group having 8 to 18, preferably 10 to 14 carbon atoms, as in the formula (II). M represents a counter ion (salt). The examples of the counter ion include alkali metal ions such as sodium and potassium, alkaline earth metal ions such as magnesium and calcium, and amines such as ammonium, monoethanolamine, diethanolamine, and triethanolamine.

Examples of the commercially available products of the imidazolinium betaine-based amphoteric surfactant include Softazoline LHL, Softazoline LHL-SF (manufactured by Kawaken Fine Chemicals Co., Ltd.), Obazoline 66N, Obazoline 66N-SF (manufactured by TOHO Chemical Industry Co., Ltd.), and Nissan Anon GLM (manufactured by NOF CORPORATION), any of which is suitably used.

It should be noted that, in the present invention, the imidazolinium betaine-based amphoteric surfactant can be used singly or in combination of the two or more.

According to the present invention, the amount of the imidazolinium betaine-based amphoteric surfactant to be blended is, as a pure ingredient, 1.5 to 12% by mass, preferably 3 to 9% by mass relative to the detergent composition. If the amount of the ingredient to be blended is less than 1.5% by mass as a pure ingredient, not only the detergent effect as a detergent composition, but also the antimicrobial activity may become insufficient. Alternatively, if the surfactant is blended more than 12% by mass, the antimicrobial activity commensurate with the amount to be blended cannot be achieved.

It should be noted that commercially available raw materials of the imidazolinium betaine-based amphoteric surfactant are usually provided in the form of an aqueous solution of the ingredients. Also in such a case, the raw material may be used such that the pure ingredient of the imidazolinium betaine-based amphoteric surfactant falls in the range of the amount to be blended. For example, in the case where a commercially available raw material is provided as an aqueous solution having a concentration of 30%, the amount to be blended in the composition of the present invention is 5 to 40% by mass, and preferably 10 to 30% by mass.

PEG-1 Lauryl Glycol

PEG-1 lauryl glycol used for the present invention is a type of alkanediol-based nonionic surfactant, and a compound represented by the following formula (I).

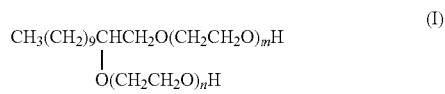

(I)

In the formula (I), m and n each represent the number of moles of added oxyethylene group, and the average of m+n is 1.

An example of the commercially available product of such PEG-1 lauryl glycol includes New Pole DDE-10 (manufactured by Sanyo Chemical Industries, Ltd.), which can be suitably used.

In the present invention, the amount of the PEG-1 lauryl glycol to be blended is 0.5 to 10% by mass, preferably 1 to 7% by mass relative to the detergent composition. If the amount of the ingredient to be blended is less than 0.5% by mass, the antimicrobial and antimycotic properties may be insufficient. If the ingredient is blended more than 10% by mass, the antimicrobial activity commensurate with the amount to be blended cannot be achieved.

PEG-1 lauryl glycol has a strong interaction with cells. Thus, it is said that PEG-1 lauryl glycol approaches cells, derives bacteria and mold of the moisture to dissolve the ingredient itself, and disables their growth. According to this, it has been known that PEG-1 lauryl glycol has an antimicrobial ability. Furthermore, the present application reveals first that, when the ingredient is used in combination with the imidazolinium betaine-based amphoteric surfactant, the antimicrobial activity of a composition obtained is significantly enhanced beyond the level expected from the amount of the ingredient blended. It should be noted that, although the antimicrobial activity is observed in the imidazolinium betaine-based amphoteric surfactant itself, the effect of the single surfactant is not sufficient. Thus, it is believed that the enhancement of the antimicrobial activity (against bacteria and fungi) in the composition is not merely due to the cumulative effect of the two ingredients and that the imidazolinium betaine-based amphoteric surfactant enhances the ability of PEG-1 lauryl glycol to thereby exert synergy.

As above described, the detergent composition of the present invention has a high antimicrobial activity against bacteria and fungi. Accordingly, by being routinely used as an ordinary detergent composition, the present invention prevents growth of the bacteria and fungi adhering to the hair and skin, and is expected for the effect of preventing infectious diseases. The detergent composition of the present invention may widely sterilize bacteria and fungi associated with infectious diseases of animals including humans, and is particularly effective for sterilizing bacteria such as *Escherichia coli* (colon bacillus), *Staphylococcus intermedius* (the pathogen of pyoderma), *Staphylococcus aureus* (a resident bacterium in the epidermis), Methicillin-resistant *Staphylococcus aureus* (a multidrug-resistant bacterium), *Staphylococcus epidermidis* (a resident bacterium in the epidermis), *Pseudomonas aeruginosa* (blue pus bacillus), *Pasteurella multocida* (the animal pasteurellosis pathogen), and *Proteus mirabilis* (the pathogen of urinary tract infection); and fungi such as *Malassezia pachydermatis* (the pathogen of otitis externa), *Microsporum canis* (a pathogen of ringworm), *Trichophyton mentagrophytes* (a pathogen of ringworm), and *Candida*, which are microorganisms observed in pet animals such as dogs and cats. Additionally, since the imidazolinium betaine-based amphoteric surfactant is highly safe for organisms and is also very low-irritant to the eyes, the surfactant is suitable as a detergent ingredient for the detergent composition of the present invention.

Alternatively, due to the microcidal effect and low in irritant properties, the detergent composition of the present invention is particularly effective for use in patients with human atopic dermatitis.

Alternatively, in the present invention, from a viewpoint of further enhancing the antimicrobial activity of the detergent composition, ingredients having a microstatic effect or microcidal effect are preferably additionally blended singly or in combination.

Ingredients having a microcidal effect that may be used in the present invention are ingredients usually used in cosmetics and quasi-pharmaceutical products, and are not particularly limited as long as they are those do not impair the safety of the composition according to the present invention or they are used in an amount that does not impair the safety. Particularly, examples of the ingredients include divalent glycols such as 1,3-butylene glycol, 1,4-butylene glycol, 2,3-butylene glycol, 2,3-dimethyl-2,3-butylene glycol, 1,3-propanediol, propylene glycol (1,2-propanediol), dipropylene glycol, and ethylene glycol, and ingredients such as hinokitiol, trichlorocarbanilide (TCC), and benzalkonium chloride. Preferred divalent glycols are 1,3-propanediol, propylene glycol, and 1,3-butylene glycol.

It should be noted that, in the case of using a divalent glycol, a sufficient microcidal effect can be achieved by blending 7% by mass or more of the glycol relative to the detergent composition of the present invention.

Alternatively, a sufficient microcidal effect can be achieved, in the case of using hinokitiol, by blending 0.001 to 0.5% by mass of hinokitiol relative to the detergent composition of the present invention, in the case of using trichlorocarbanilide (TCC), by blending 0.01 to 1% by mass of TCC relative to the detergent composition of the present invention, and in the case of using benzalkonium chloride, by blending 0.01 to 2% by mass of benzalkonium chloride relative to the detergent composition of the present invention.

Alternatively, in the present invention, as the anionic surfactant to be a detergent ingredient, particularly, a compound selected from acyl taurates, acyl methyltaurates, and acyl glutamates is preferably blended.

Examples of acyl taurates include coconut oil fatty acid (cocoyl) taurate, lauroyl taurate, myristoyl taurate, palmitoyl taurate, and stearoyl taurate.

Examples of acyl methyltaurates include coconut oil fatty acid (cocoyl) methyltaurate, lauroyl methyltaurate, myristoyl methyltaurate, palmitoyl methyltaurate, and stearoyl methyltaurate.

Examples of acyl glutamates include coconut oil fatty acid (cocoyl) glutamate, lauroyl glutamate, myristoyl glutamate, palmitoyl glutamate, and stearoyl glutamate.

It should be noted that examples of each of the salt include sodium salts, potassium salts, magnesium salts, and triethanolamine salts.

Of the anionic surfactants, lauroyl methyltaurate, coconut oil fatty acid (cocoyl) methyltaurate, lauroyl glutamate, and/or coconut oil fatty acid (cocoyl) glutamate are preferred, and each suitable counter ion is sodium or potassium.

The anionic surfactants are extremely safe for organisms, and additionally, the antimicrobial activity of the present invention is not decreased if the surfactants are blended. Therefore, the surfactants are suitable as the detergent ingredients of the present invention. The amount of the ingredients to be blended may be the amount usually used in a detergent composition, and particularly, as a pure ingredient, the range of 1.5 to 7.5% by mass is preferred. Blending of less than 1.5% by mass, as a pure ingredient, may be insufficient in the detergent effect and foaming properties, and blending of more than 7.5% by mass may cause a squeaky feeling on hair coats during drying after the detergent composition is used.

It should be noted that commercially available raw materials of the anionic surfactant may be provided as an aqueous solution of the ingredients. Also in such a case, the pure ingredient of the anionic surfactant may be adjusted to fall within the range of the amount to be blended. For example, in the case where a commercially available raw material is provided as an aqueous solution having a concentration of 30%, the amount to be blended in the composition of the present invention is 5 to 25% by mass.

To the detergent composition according to the present invention, in addition to the ingredients, it is possible to blend the following ingredients usually used in detergent compositions of cosmetics or quasi-pharmaceutical products to the extent that the effect of the present invention is not impaired. The detergent composition of the present invention can be prepared by blending the suitable ingredients and/or the following ingredients to an imidazolinium betaine-based amphoteric surfactant and PEG-1 lauryl glycol, which are the essential ingredients, as appropriate according to the conventional method.

Examples of the humectant include polyethylene glycol, propylene glycol, glycerin, 1,3-butylene glycol, xylitol, sorbitol, maltitol, chondroitin sulfate, hyaluronic acid, mucoitinsulfuric acid, caronic acid, atelocollagen, cholesteryl-12-hydroxystearate, sodium lactate, bile salt, dl-pyrrolidone carboxylate, short-chain soluble collagen, diglycerin (EO) PO adduct, chestnut rose extract, yarrow extract, and melilot extract.

Examples of the color material include organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, Blue No. 404, Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3 and Blue No. 1; and natural colorants such as chlorophyll and β-carotene.

Examples of liquid oils and fats include avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cotton seed oil, perilla oil, soybean oil, groundnut oil, tea oil, Japanese torreya nuts oil, rice bran oil, Chinese tung oil, Japanese tung oil, jojoba oil, germ oil, and triglycerol.

Examples of higher alcohols include linear alcohols such as lauryl alcohol, cetyl alcohol, stearyl alcohol, behenyl alcohol, myristyl alcohol, oleyl alcohol and cetostearyl alcohol; and branched-chain alcohols such as monostearylglycerin ether (batyl alcohol), 2-decyltetradecanol, lanolin alcohol, cholesterol, phytosterol, hexyldodecanol, isostearyl alcohol and octyldodecanol.

Examples of ester oils include isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxy stearate, ethylene glycol di-2-ethyl hexanoate, dipentaerythritol fatty acid ester, N-alkyl glycol monoisostearate, neopentyl glycol dicaprate, diisostearyl malate, glycerol di-2-heptyl undecanoate, trimethylol propane tri-2-ethyl hexanoate, trimethyrol propane triisostearate, pentaerythritol tetra-2-ethyl hexanoate, glycerol tri-2-ethyl hexanoate, glycerol trioctanoate, glycerol triisopalmitate, trimethyrol propane triisostearate, cetyl 2-ethyl hexanoate, 2-ethylhexyl palmitate, glycerol trimyristate, glyceride tri-2-heptyl undecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-hexyldecyl sebacate, 2-hexyldecyl adipate, diisopropyl sebacate, 2-ethylhexyl succinate, and triethyl citrate.

Examples of silicone oils include chain polysiloxanes such as dimethylpolysiloxane, methylphenylpolysiloxane and diphenylpolysiloxane; cyclic polysilocanes such as octamethylcyclotetrasiloxane, decamethylcyclopentasiloxane and dodecamethylcyclohexasiloxane; silicone resin having a three dimensional network structure; silicone rubber; various modified polysiloxanes such as amino-modified polysiloxane, polyether-modified polysiloxane, alkyl-modified polysiloxane and fluorine-modified polysiloxane; and acrylic silicone.

Examples of natural water-soluble polymers include plant-derived polymers such as gum Arabic, tragacanth gum, galactan, guar gum, carob gum, karaya gum, carrageenan, pectin, agar, quince seed (*Cydonia oblonga*), algae colloid (brown algae extract) and starch (rice, corn, potato and wheat); microbially-derived polymers such as xanthane gum, dextran, succinoglycan and pullulan; animal-derived polymers such as collagen, casein, albumin and gelatin.

Examples of semisynthetic water-soluble polymers include starch-based polymers such as carboxymethyl starch and methylhydroxypropyl starch; cellulose-based polymers such as methyl cellulose, ethylcellulose, methylhydroxypropylcellulose, hydroxyethylcellulose, sodium cellulose sulfate, hydroxypropylcellulose, carboxymethylcellulose, sodium carboxymethyl cellulose, microcrystalline cellulose and cellulose powder; alginic acid-based polymers such as sodium alginate and propylene glycol alginate ester; cationized cellulose; cationized guar gum; cationized starch; and cationized fenugreek gum.

Examples of synthetic water-soluble polymers include vinyl-based polymers such as polyvinyl alcohol, polyvinyl methyl ether, polyvinylpyrrolidone and carboxy vinyl polymer; polyoxyethylene-based polymers such as polyethylene glycol 20,000, 40,000 and 60,000; acrylic-based polymers such as sodium polyacrylate, polyethyl acrylate and polyacrylamide; polyethylenimine; Polyquaternium-51; Polyquaternium-6; Polyquaternium-7; Polyquaternium-22; Polyquaternium-39; Polyquaternium-47; and Polyquaternium-53.

Examples of thickeners other than the above water-soluble polymers include dextrin, sodium pectate, locust bean gum, tamarind gum, dialkyl dimethyl ammonium cellulose sulfate, magnesium aluminum silicate, bentonite, hectorite, laponite, and anhydrous silicic acid.

Examples of UV absorbers include benzoic acid-based UV absorbers such as p-aminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester and N,N-dimethyl PABA butyl ester; anthranilic acid-based UV absorbers such as homomenthyl N-acetyl anthranilate; salicylic acid-based UV absorbers such as amyl salicylate, menthyl salicylate, homomenthyl salicylate, octyl salicylate, phenyl salicylate, benzyl salicylate and p-isopropanolphenyl salicylate; cinnamic acid-based UV absorbers such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate and glyceryl mono-2-ethylhexanoyl-diparamethoxycinnamate; benzophenone-based UV absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate, 2-hydroxy-4-n-octoxybenzophenone and 4-hydroxy-3-carboxybenzophenone; 3-(4'-methylbenzylidene)-d,l-camphor; 3-benzylidene-d,l-camphor; 2-phenyl-5-methylbenzoxazol; 2,2'-hydroxy-5-methylphenylbenzotriazol; 2-(2'-hydroxy-5'-t-octylphenyl)benzotriazol; 2-(2'-hydroxy-5-methylphenyl)benzotriazol; dibenzalazine; dianisoylmethane; 2-methoxy-2'-t-butyl dibenzoylmethane; and 5-(3,3-dimethyl-2-norbornyl)-3-pentane-2-one.

Examples of lower alcohols include ethanol, propanol, isopropanol, isobutyl alcohol and t-butyl alcohol.

Examples of polyhydric alcohols include ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol, glycerin, trimethylolpropane, 1,2,6-hexanetriol, xylitol, sorbitol, mannitol, diethylene glycol, dipropylene glycol, triethylene glycol, polypropylene glycol, tetraethylene glycol, diglycerol, polyethylene glycol, triglycerol, tetraglycerol, polyglycerol, ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, ethylene glycol dibutyl ether, diethylene glycol monomethyl ether, diethylene glycol monoethyl ether, diethylene glycol monobutyl ether, diethylene glycol dimethyl ether, diethylene glycol diethyl ether, diethylene glycol dibutyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether, ethylene glycol monomethyl ether acetate, ethylene glycol monoethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate, chimyl alcohol, selachyl alcohol, batyl alcohol, sorbitol, maltitol, moltotriose, mannitol, erythritol, fructose, starch sugar, maltose, xylitol, starch sugar reduced alcohol, glysolid, tetrahydrofurfuryl alcohol, POE tetrahydrofurfuryl alcohol, POP butyl ether, POP/POE butyl ether, tripolyoxypropylene glycerin ether, POP glycerol ether, POP glycerol ether phosphate, POP/POE pentaerythritol ether, and polyglycerol.

Examples of monosaccharides include D-glyceryl aldehyde, dihydroxyacetone, D-erythrose, D-erythrulose, D-threose, erythritol, L-arabinose, D-xylose, L-lyxose, D-arabinose, D-ribose, D-ribulose, D-xylulose, L-xylulose, D-glucose, D-talose, D-psicose, D-galactose, D-fructose, L-galactose, L-mannose, D-tagatose, heptose, octulose, 2-deoxy-D-ribose, 6-deoxy-L-galactose, 6-deoxy-L-mannose, D-glucosamine, D-galactosamine, sialic acid, aminouronic acid, muramic acid, D-glucuronic acid, D-mannuronic acid, L-glucuronic acid, D-galacturonic acid, and L-iduronic acid.

Examples of oligosaccharides include sucrose, gentianose, umbelliferose, lactose, planteose, isolychnoses, α,α-trehalose, raffinose, lychnoses, umbilicin, stachyose, and verbascoses, Examples of amino acids include neutral amino acids such as threonine and cysteine; and basic amino acids such as hydroxylysine. Also, Examples of amino-acid derivatives include sodium acyl sarcosinate (sodium lauroyl sarcosinate), acyl glutamate, acyl β-alanine sodium salt, glutathione, and pyrrolidone carboxylate.

Examples of sequestering agents include 1-hydroxyethane-1,1-diphosphonic acid, tetrasodium 1-hydroxyethane-1,1-diphosphonate, disodium edetate, trisodium edetate, tetrasodium edetate, sodium citrate, sodium polyphosphate, sodium metaphosphate, gluconic acid, malic acid, citric acid, ascorbic acid, succinic acid, edetic acid, hydroxyethylethylenediamine triacetic acid trisodium salt, and tetrasodium etidronate.

Examples of antioxidants include phosphoric acid, citric acid, ascorbic acid, maleic acid, malonic acid, succinic acid, fumaric acid, cephalin, hexametaphosphate, phytic acid, and ethylenediaminetetraacetate.

Also, various surfactants other than listed above may be added to a detergent composition of the present invention within a scope which does not impair the effects of the invention.

Examples of anionic surfactants include fatty acid soaps such as sodium laurate and sodium palmitate; higher alkyl sulfates such as sodium lauryl sulfate, potassium lauryl sulfate; alkyl ether sulfates such as triethanolamine POE lauryl ether sulfate; phosphate esters such as sodium POE oleyl ether phosphate and POE stearyl ether phosphate; sulfosuccinates such as sodium di(2-ethylhexyl)sulfosuccinate, sodium monolauroyl monoethanolamide polyoxyethylene sulfosuccinate and sodium lauryl polypropylene glycol sulfosuccinate; alkylbenzene sulfonates such as sodium dodecylbenzene sulfonate (linear), triethanolamine dodecylbenzene sulfonate (linear) and dodecylbenzenesulfonic acid (linear); higher fatty acid ester sulfates such as hydrogenated coconut oil fatty acid glycerin sodium sulfate; N-acylglutamates such as monosodium N-lauroyl glutamate, disodium N-stearoyl glutamate and monosodium N-myristoyl-L-glutamate; sulfate oils such as Turkey red oil; POE alkyl ether carboxylic acid; POE alkylaryl ether carboxylate; α-olefin sulfonate; higher fatty acid ester sulfonate; secondary alcohol sulfate; higher fatty acid alkylol amide sulfate; sodium lauroyl monoethanolamide succinate; ditriethanolamine N-palmitoyl aspartate; and casein sodium.

Examples of lipophilic nonionic surfactants include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate; glycerol polyglycerol fatty acid esters such as glycerol mono-cottonseed oil fatty acid ester, glycerol monoerucate, glycerol sesquioleate, glycerol monostearate, glycerol α,α'-oleate pyroglutamate and glycerol monostearate malate; propylene glycol fatty acid esters such as propylene glycol monostearate; hydrogenated castor oil derivatives; and glycerol alkyl ethers.

Examples of hydrophilic nonionic surfactants include POE sorbitan fatty acid esters such as POE sorbitan monooleate, POE sorbitan monostearate, POE sorbitan monooleate and POE sorbitan tetraoleate; POE sorbitol fatty acid ester such as POE sorbitol monolaurate, POE sorbitol monooleate, POE sorbitol pentaoleate and POE sorbitol monostearate; POE glycerol fatty acid esters such as POE glycerol monostearate, POE glycerol monoisostearate and POE glycerol triisostearate; POE fatty acid esters such as POE distearate, POE monodioleate and ethylene glycol distearate; POE alkyl ethers such as POE lauryl ether, POE oleyl ether, POE stearyl ether, POE behenyl ether, POE 2-octyldodecyl ether and POE cholestanol ether; pluronic types such as Pluronic; POE/POP alkyl ethers such as POE/POP cetyl ether, POE/POP 2-decyltetradecyl ether, POE/POP monobutyl ether, POE/POP hydrogenated lanolin and POE/POP glycerol ether; tetra POE/POP ethylenediamine condensates such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamate monoisostearate diester and POE hydrogenated castor oil maleate; POE beeswax/lanolin derivatives such as POE sorbitol beeswax ester; alkanolamides such as coconut oil fatty acid diethanolamide, coconut oil fatty acid monoethanolamide, lauric acid monoethanolamide and fatty acid isopropanolamide; POE propylene glycol fatty acid ester; POE alkylamine; POE fatty acid amide; sucrose fatty acid ester; alkyl ethoxy dimethyl amine oxide; and trioleyl phosphate.

Examples of ampholytic surfactants include amide propyl betaines such as coconut oil fatty acid amide propyl betaine, lauric acid amide propyl betaine, myristic acid amide propyl betaine and palm kernel oil fatty acid amide propyl betaine; amide sulphobetaines such as lauryl amidopropyl hydroxyl sulphobetaine; amide amine oxide such as lauryl amidopropyl dimethyl amine oxide; and carbobetaines such as hydroxyl alkyl (C12-14) hydroxyethyl methyl glycine.

Examples of other components which may be blended include preservatives such as ethylparaben and butylparaben; whitening agents such as vitamin C derivative, saxifrage extract and arbutin; blood circulation promoters such as nicotinic acid, benzyl nicotinate, tocopherol nicotinate, nicotinic acid β-butoxy ester, minoxidil or its analogs, vitamin E group, γ-orizanol, alkoxycarbonyl pyridine N-oxide, carpronium chloride and acetylcholine or its derivatives; various extracts such as ginger, *phellodendron amurense, coptis chinensis* rhizome, *lithospermum* root, birch, loquat, carrot, aloe, mallow, iris, grape, loofah, lily, saffron, *cnidium officinale* root, ginger, hypericum, *ononis spinosa* root, garlic, capsicum, citrus unshiu peel, *angelica acutiloba* root, peony and seaweed; activator agents such as panthenyl ethyl ether, nicotinic-acid amide, biotin, pantothenic acid, royal jelly and cholesterol derivatives; antiseborrheic agents such as pyridoxine and thianthol.

The detergent composition according to the present invention can be used for human skin and hair as well as for cleaning of hair coats of animals such as dogs and cats. Although usage forms of the detergent composition of the present invention are not particularly limited, for example, usages as foot detergents based on a disinfection effect on *Trichophyton*, detergents for particular microbe based on sterilization of *Candida* and the like, body detergents having a deodorant effect based on a microcidal effect on microbe derived from the epidermis, detergents for atopy based on a microcidal effect on *Staphylococcus aureus* and *Pseudomonas aeruginosa*, hand soaps, detergents for tableware, and detergents for food are contemplated. Alternatively, the compositions of the present invention, which are widely effective for microbe adhering to animal hair coats, can be suitably used as, particularly, detergent compositions for animals such as shampoos for animals. Additionally, the composition is suitable as a detergent composition for patients with human atopic dermatitis.

Alternatively, dosage forms of the detergent composition according to the present invention are not particularly limited, and for example, concentrated type detergent compositions, which are used after dilution, are also included in the present invention.

According to the formulation in the following Table 1, the detergent composition of each Test Example was prepared in accordance with the conventional method. Each prepared detergent composition was evaluated for its antimicrobial activity in accordance with the following test method. The results are shown in Table 1.

<Test Method>

Each 2 mL of various bacterial solutions of *Pseudomonas aeruginosa, Escherichia coli, Staphylococcus aureus*, and *Candida* ($2\times10^4$/mL, sterilized distilled water) and 2 mL of the detergent composition of each Test Example were mixed to set the final bacterial concentration of the mixed solution to $1\times10^4$/mL. Subsequently, the resulting mixed solution was reacted in dark at room temperature for 15, 30, and 60 minutes. After the reaction, each mixed solution was diluted 10 fold with sterilized distilled water. After 0.1 mL of the solution was smeared on each medium and cultured, the viable cell count was determined. The media and culture conditions were set to 30° C. for 24 hours on an agar standard medium for bacteria and 25° C. for 48 hours on a Sabouraud agar medium for fungi.

Depending on the determined viable cell count, each composition was assessed for antimicrobial and antimycotic abilities against each microbial strain in accordance with the following evaluation criteria.

Evaluation Criteria of Antimicrobial Activity

⊚: The viable cell count decreased to substantially zero within 15 minutes.

○: An obvious decreasing trend of the viable cell count was observed within 60 minutes (1/100).

Δ: A gradual decreasing trend of the viable cell count was observed within 60 minutes (1/10).

x: Decrease in the viable cell count was not observed.

TABLE 1

|  | Test Example | | | | |
| --- | --- | --- | --- | --- | --- |
|  | 1-1 | 1-2 | 1-3 | 1-4 | 1-5 |
| Sodium undecyl hydroxyethyl imidazolinium betaine solution (27%) (*1) (Sodium N-lauroyl-N'-carboxymethyl-N'-hydroxyethyl ethylenediamine solution) | 15 | — | 15 | 15 | — |
| Coconut oil fatty acid amidodimethyl aminoacetic acid betaine solution (*2) | — | — | — | — | 15 |
| PEG-1 lauryl glycol (*3) | — | 2 | 2 | 2 | 2 |
| 1,3-propanediol | — | — | — | 5 | 5 |
| Propylene glycol | — | — | — | 5 | 5 |
| Water | Balance | Balance | Balance | Balance | Balance |
| [Antimicrobial activity] | | | | | |
| *Pseudomonas aeruginosa* | ⊚ | X | ⊚ | ⊚ | X |
| *Escherichia coli* | ○ | X | ⊚ | ⊚ | X |
| *Staphylococcus aureus* | X | ○ | Δ | ○ | X |
| *Candida* | X | X | Δ | Δ | X |

(*1): Softazoline LHL-SF (manufactured by Kawaken Fine Chemicals Co., Ltd.)
(*2): Lebon 2000-SF (manufactured by Sanyo Chemical Industries, Ltd.)
(*3): New Pole DDE-10 (manufactured by Sanyo Chemical Industries, Ltd.)

Examples

Hereinbelow, the present invention is described in more detail referring to Examples, but the present invention is not intended to be limited to these. It should be noted that all the numeric values represent % by mass, unless specifically specified (in the case of representing a raw material (product) name, % by mass of the raw material is represented.)

As shown in Table 1, Test Example 1-1, in which an imidazolinium betaine-based amphoteric surfactant (an aqueous solution of sodium N-lauroyl-N'-carboxymethyl-N'-hydroxyethylethylenediamine) was blended, was effective in sterilization of *Pseudomonas aeruginosa* and *Escherichia coli* when used alone, but in Test Example 1-'), in which PEG-1 lauryl glycol was blended, no microcidal effect on the bacteria other than *Staphylococcus aureus* was observed.

However, in Test Example 1-3, in which the imidazolinium betaine-based surfactant and the PEG-1 lauryl glycol, which showed almost no disinfection effect when used alone, were combined, an enhanced microcidal effect on *Escherichia coli* and *Candida* was observed.

Furthermore, for the composition of Test Example 1-4, in which divalent glycols including 1,3-propanediol and propylene glycol were blended, an enhanced microcidal effect on *Staphylococcus aureus* was observed compared to Test Example 1-3.

In contrast, in Test Example 1-5, in which the imidazolinium betaine-based amphoteric surfactant was replaced with other surfactant (a coconut oil fatty acid amidodimethyl aminoacetic acid betaine solution), a sufficient microcidal effect was not achieved on all the bacterial strains.

From the above, as the composition according to the present invention, a combination of the imidazolinium betaine-based amphoteric surfactant and PEG-1 lauryl glycol is preferred, and addition of divalent glycols to further increase the antimicrobial activity is also preferred.

Additionally, using the test method and evaluation criteria similar to the above, the detergent compositions of the formulation shown in the following Table 2 were also reviewed for the antimicrobial activity. The results are shown in Table 2.

blending sodium coconut oil fatty acid methyl taurate and potassium cocoyl glutamate as the detergent ingredients, the antimicrobial activity of the composition was not substantially influenced, and the similar trend in the blend effect of the essential ingredients to Table 1 was shown (Test Examples 2-1 to 2-4). It should be noted that, in Table 2, coconut oil fatty acid diethanolamide, which is a nonionic surfactant, was also blended, but the influence due to the ingredient on the antimicrobial activity was not observed.

Alternatively, in Test Example 2-5, in which hinokitiol was further blended as an ingredient having a microcidal effect, the antimicrobial activity of the composition was further enhanced (Test Example 2-5).

Accordingly, in the present invention, it is possible to use acyl methyl taurates and acyl glutamates as detergent ingredients that do not influence on the antimicrobial activity of the composition and are highly safe.

Additionally, using the test method and evaluation criteria similar to the above, the detergent compositions of the formulation shown in the following Table 3 were also reviewed

TABLE 2

|  | Test Example | | | | |
| --- | --- | --- | --- | --- | --- |
|  | 2-1 | 2-2 | 2-3 | 2-4 | 2-5 |
| Sodium N-lauroyl-N'-carboxymethyl-N'-hydroxyethyl ethylenediamine solution (27%) (*1) | — | 15 | — | 15 | 15 |
| PEG-1 lauryl glycol (*3) | — | — | 2 | 2 | 2 |
| 1,3-propanediol | 5 | 5 | 5 | 5 | 5 |
| Hinokitiol | — | — | — | — | 0.1 |
| Sodium coconut oil fatty acid methyl taurate solution (30%) (*4) | 10 | 10 | 10 | 10 | 10 |
| Potassium cocoyl glutamate solution (30%) (*5) | 5 | 5 | 5 | 5 | 5 |
| Coconut oil fatty acid diethanolamide (*6) | 2 | 2 | 2 | 2 | 2 |
| Propylene glycol | 5 | 5 | 5 | 5 | 5 |
| Water | Balance | Balance | Balance | Balance | Balance |
| [Antimicrobial activity] | | | | | |
| *Pseudomonas aeruginosa* | X | ◎ | X | ◎ | ◎ |
| *Escherichia coli* | X | ○ | Δ | ◎ | ◎ |
| *Staphylococcus aureus* | X | X | Δ | ○ | ◎ |
| *Candida* | X | X | X | Δ | ◎ |

(*1): Softazoline LHL-SF (manufactured by Kawaken Fine Chemicals Co., Ltd.)
(*3): New Pole DDE-10 (manufactured by Sanyo Chemical Industries, Ltd.)
(*4): ST-SF Super (manufactured by NOF Corporation)
(*5): Amisoft CK-22 (manufactured by Ajinomoto Co., Inc.)
(*6): Amizole CDE (manufactured by Kawaken Fine Chemicals Co., Ltd.)

As shown in Table 2, for the suitable ingredient composition of the present invention shown in Table 1, in the case of for the antimicrobial activity. The results are shown in Table 3.

TABLE 3

|  | Test Example | | | | | | | |
| --- | --- | --- | --- | --- | --- | --- | --- | --- |
|  | 1 | 2 | 3 | 4 | 5 | 6 | 7 | 8 |
| Sodium undecyl hydroxyethyl imidazolinium betaine solution (27%) (Softazoline LHL-SF manufactured by Kawaken Fine Chemicals Co., Ltd.) | 15 | — | — | — | — | — | — | — |
| Sodium coconut oil fatty acid methyl taurate solution (30%) (ST-SF Super manufactured by NOF Corporation) | — | 15 | — | — | — | — | — | — |
| Sodium cocoyl glutamate solution (24.2%) (Amisoft CS-22 manufactured by Ajinomoto Co., Inc.) | — | — | 15 | — | — | — | — | — |
| Sodium POE (2) lauryl ether sulfate solution (27%) (Alscope NS230 manufactured by TOHO Chemical Industry Co., Ltd.) | — | — | — | 15 | — | — | — | — |

TABLE 3-continued

|  | Test Example | | | | | | | |
|---|---|---|---|---|---|---|---|---|
|  | 1 | 2 | 3 | 4 | 5 | 6 | 7 | 8 |
| Lauryl dimethyl amino acetic acid betaine solution (40%) (Nissananon BL-SF manufactured by NOF Corporation) | — | — | — | — | 15 | — | — | — |
| Lauryl amidopropyl dimethyl amine oxide solution (30%) (Softazoline LAO-C manufactured by Kawaken Fine Chemicals Co., Ltd.) | — | — | — | — | — | 15 | — | — |
| Sodium POE lauryl ether acetate solution (NIKKOL AKYPO RLM 45 NV manufactured by Nikko Chemicals Co., Ltd.) | — | — | — | — | — | — | 15 | — |
| Sodium lauroyl β-alanine solution (30%) (NIKKOL Alaninate LN-30 manufactured by Nikko Chemicals Co., Ltd.) | — | — | — | — | — | — | — | 15 |
| PEG-1 lauryl glycol (Newpol DDE-10 manufactured by Sanyo Chemical Industries, Ltd. | 2 | 2 | 2 | 2 | 2 | 2 | 2 | 2 |
| Water | Balance | Balance | Balance | Balance | Balance | Balance | Balance | Balance |
| [Antimicrobial activity] | | | | | | | | |
| Pseudomonas aeruginosa | ⊚ | X | X | X | X | X | X | X |
| Escherichia coli | ⊚ | X | X | X | X | X | X | X |
| Staphylococcus aureus | Δ | X | X | X | X | X | X | X |
| Candida | Δ | X | X | X | X | X | X | X |

In Table 3, sodium coconut oil fatty acid methyl taurate (a nitrogen-containing anionic surfactant), sodium cocoyl glutamate (a nitrogen-containing anionic surfactant), sodium POE(2) lauryl ether sulphate (an anionic surfactant), lauryl dimethyl aminoacetic acid betaine (a nitrogen-containing amphoteric surfactant), lauryl amidopropyl dimethylamine oxide (a nitrogen-containing amphoteric surfactant), sodium POE lauryl ether acetate (an anionic surfactant) and sodium lauroyl-β-alanine (a nitrogen-containing anionic surfactant) are common surfactants used in detergent compositions.

As shown in Table 3, PEG-1 lauryl glycol showed a synergic effect only with the imidazolinium betaine-based amphoteric surfactant (Test Example 1).

In any of Test Examples 2 to 8, in which other surfactants were blended, the antimicrobial activity greater than that of Test Example 1 was not observed. Additionally, even the antimicrobial activity observed in the case of singly using PEG-1 lauryl glycol (Test Example 1-2 in Table 1) was canceled, and the antimicrobial effect rather tended to be eliminated.

Accordingly, in the composition according to the present invention, along with PEG-1 lauryl glycol, it is particularly suitable to use the imidazolinium betaine-based amphoteric surfactant.

Furthermore, the detergent composition of the present invention was reviewed for the effectivity as a body detergent for human (for the hair, face, and body).

The detergent compositions of the formulation shown in the following Table 3 were prepared, and safety confirmation test was conducted at first on six healthy volunteers.

<Test Method>

After an appropriate amount of the detergent composition of the formulation shown in the following Table 4 was taken in a hand or on a towel, and the body (the body, face and hair) was cleaned as usual every day for 10 days, the composition was evaluated for its safety in accordance with the following evaluation criteria. The results are shown in Table 5.

TABLE 4

| (Component) | (% by mass) |
|---|---|
| Sodium N-lauroyl-N'-carboxymethyl-N'-hydroxyethyl ethylenediamine solution (27%) (*1) | 30 |

TABLE 4-continued

| (Component) | (% by mass) |
|---|---|
| PEG-1 lauryl glycol (*3) | 2 |
| 1,3-propanediol | 5 |
| Sodium coconut oil fatty acid methyl taurate solution (30%) (*4) | 15 |
| Potassium cocoyl glutamate solution (30%) (*5) | 10 |
| Coconut oil fatty acid diethanolamide (*6) | 2 |
| Propylene glycol | 8 |
| Water | Balance |

(*1): Softazoline LHL-SF (manufactured by Kawaken Fine Chemicals Co., Ltd.)
(*3): New Pole DDE-10 (manufactured by Sanyo Chemical Industries, Ltd.)
(*4): ST-SF Super (manufactured by NOF Corporation)
(*5): Amisoft CK-22 (manufactured by Ajinomoto Co., Inc.)
(*6): Amizole CDE (manufactured by Kawaken Fine Chemicals Co., Ltd.)

Evaluation Criteria of Safety

During the actual use test, the incidence of troubles (tingling, itch, glow, swelling, peeling of skin, chapping, eczema, irritation, itch, redness, ache, dandruff and others) on the skin (face skin, scalp, and body skin) and in the eyes, respectively, was evaluated by an assessing doctor in accordance with the following criteria, and the number of the volunteers of each evaluation was totaled.

⊚: During the actual use, there was no trouble on the skin (the face skin, scalp, and body skin) or in the eyes.

x: During the actual use, a trouble occurred on the skin (the face skin, scalp, and body skin) or in the eyes.

TABLE 5

|  | Number of respondents | |
|---|---|---|
|  | ⊚ | X |
| Incidence of troubles on the face skin during the actual use | 6 | 0 |
| Incidence of troubles in the eyes during the actual use | 6 | 0 |
| Incidence of troubles on the scalp during the actual use | 6 | 0 |
| Incidence of troubles on the body skin during the actual use | 6 | 0 |

As shown in Table 5, in the actual use test by healthy individuals, it was confirmed that there was no problem in the safety of the detergent composition. Subsequently, on six male volunteers in their thirties having symptoms of atopic dermatitis (AD), an actual use test of the detergent composition of the present invention (the detergent composition of the formulation shown in Table 4) was conducted as follows.

<Test Method>

After an appropriate amount was taken in a hand or on a towel and the body (body, face and hair) was cleaned as usual every day for one month or three months, the subject sites were evaluated for the improvement in the effect by an assessing doctor in accordance with the following criteria, and the number of the volunteers of each evaluation was totaled. Additionally, whether troubles on skin (face skin, scalp, and body skin) and in the eyes during use were present or not was evaluated in accordance with the evaluation criteria of safety. The results are shown in Table 6.

Evaluation Criteria of the Improvement in the Effect

☉: On the subject site, any of itch, chapping, redness, hypertrophy, and pigmentation of skin was improved.

Δ: On the subject site, there was no change in the symptoms.

x: On the subject site, any of itch, chapping, redness, hypertrophy, and pigmentation became worse.

TABLE 6

|  | Number of respondents | | |
|---|---|---|---|
|  | ☉ | Δ | X |
| Improvement in the effect after one month of use | 5 | 1 | 0 |
| Improvement in the effect after three months of use | 5 | 1 | 0 |
| Incidence of troubles during the actual use | 6 | — | 0 |

As shown in Table 6, it was revealed that the detergent composition of the present invention can be used on the skin of atopic dermatitis (AD) without causing troubles, and that the improving effect on AD is promising.

AD facilitates growth of bacteria such as *Staphylococcus aureus* and *Pseudomonas aeruginosa* on the skin, and may cause itch and inflammation. The detergent composition of the present invention, which has a high disinfection effect as previously shown and contains ingredients having low irritant properties to the skin and eyes, is considered to be effective to the subjects having AD.

What is claimed is:

1. A detergent composition comprising:
   3 to 9% by mass of an imidazolinium betaine-based amphoteric surfactant; and
   0.5 to 10% by mass of PEG-1 lauryl glycol represented by the following formula (I):

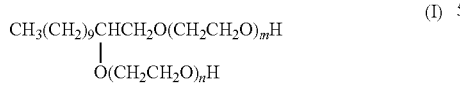

(I)

wherein, m and n each represent the number of moles of added ethylene oxide and the average of m+n is 1.

2. The detergent composition according to claim 1, further comprising an ingredient having a microstatic effect or microcidal effect selected from divalent glycols, hinokitiol, trichlorocarbanilide, and benzalkonium chloride.

3. The detergent composition according to claim 2, wherein the divalent glycols are included in the detergent composition at 7% by mass or more relative to the detergent composition.

4. The detergent composition according to claim 3, wherein the divalent glycols comprise one or more of 1,3-butylene glycol, 1,4-butylene glycol, 2,3-butylene glycol, 2,3-dimethyl-2,3-butylene glycol, 1,3-propanediol, propylene glycol (1,2-propanediol), dipropylene glycol, and ethylene glycol.

5. The detergent composition according to claim 4, wherein the divalent glycols comprise one or more of 1,3-propanediol, propylene glycol, and 1,3-butylene glycol.

6. The detergent composition according to claim 2, wherein the hinokitiol is included in the detergent composition at 0.001 to 0.5% by mass or more relative to the detergent composition.

7. The detergent composition according to claim 2, wherein the trichlorocarbanilide is included in the detergent composition at 0.01 to 1% by mass or more relative to the detergent composition.

8. The detergent composition according to claim 2, wherein benzalkonium chloride is included in the detergent composition at 0.01 to 2% by mass or more relative to the detergent composition.

9. The detergent composition according to claim 1, wherein the detergent composition is used for animals.

10. The detergent composition according to claim 1, wherein the detergent composition is used for patients with human atopic dermatitis.

11. The detergent composition according to claim 1, wherein the PEG-1 lauryl glycol represented by formula (I) is included at 1 to 7% by mass of the detergent composition.

12. The detergent composition according to claim 1, wherein the imidazolinium betaine-based amphoteric surfactant is selected from one or more of N-lauroyl-N'-carboxymethyl-N'-hydroxyethylethyleneimidazoliniumbetaine, N-cocoyl-N'-carboxymethyl-N'-hydroxyethylethyleneimidazoliniumbetaine, 2-cocoyl-N-carboxymethyl-N-hydroxyethylimidazoliniumbetaine, 2-lauryl-N-carboxymethyl-N-hydroxyethylimidazoliniumbetaine, and 2-undecyl-N,N,N-(hydroxyethylcarboxymethyl)-2-imidazoliniumbetaine, or a salt thereof.

13. The detergent composition according to claim 1, further comprising 1.5 to 7.5% by mass of an anionic surfactant, or salt thereof, selected from acyl taurates, acyl methyltaurates, and acyl glutamates.

14. The detergent composition according to claim 13, wherein the anionic surfactant includes lauroyl methyltaurate, coconut oil fatty acid (cocoyl) methyltaurate, lauroyl glutamate, coconut oil fatty acid (cocoyl) glutamate, and combinations thereof.

15. The detergent composition according to claim 1, further comprising an additive selected from humectants, pigments, oils, fats, alcohols, ester oils, silicone oils, water-soluble polymers, thickeners, UV absorbers, polyhydric alcohols, monosaccharides, oligosaccharides, amino acids, sequestering agents, surfactants, preservatives, and combinations thereof.

* * * * *